United States Patent
Langford

(10) Patent No.: US 7,323,149 B2
(45) Date of Patent: Jan. 29, 2008

(54) SUPPLEMENTAL OZONE TREATMENT FOR ENSURING THE STERILITY OF INSTRUMENT CLEANING SYSTEMS

(75) Inventor: Terrence R. Langford, Tucson, AZ (US)

(73) Assignee: Langford IC Sysstems, Inc., Tucson, AZ (US)

( * ) Notice: Subject to any disclaimer, the term of this patent is extended or adjusted under 35 U.S.C. 154(b) by 0 days.

(21) Appl. No.: 10/552,878

(22) PCT Filed: Jan. 16, 2004

(86) PCT No.: PCT/US2004/001092
§ 371 (c)(1), (2), (4) Date: Oct. 12, 2005

(87) PCT Pub. No.: WO2004/094001
PCT Pub. Date: Nov. 4, 2004

(65) Prior Publication Data
US 2006/0272682 A1    Dec. 7, 2006

(30) Foreign Application Priority Data
Apr. 18, 2003   (WO) ............... PCT/US03/12027

(51) Int. Cl.
*A61L 9/00* (2006.01)
(52) U.S. Cl. ............... 422/294; 422/301; 210/760; 210/764; 210/765; 510/383
(58) Field of Classification Search ............. None
See application file for complete search history.

(56) References Cited

U.S. PATENT DOCUMENTS

| | | | |
|---|---|---|---|
| 5,443,801 A | 8/1995 | Langford | |
| 5,520,893 A | 5/1996 | Kasting, Jr. et al. | |
| 5,567,444 A | 10/1996 | Hei et al. | |
| 5,711,921 A | * 1/1998 | Langford | 422/292 |
| 6,027,688 A | 2/2000 | Wainwright | |
| 6,096,266 A | 8/2000 | Duroselle | |
| 6,358,478 B1 | 3/2002 | Soremark | |
| 6,387,241 B1 | 5/2002 | Murphy et al. | |

(Continued)

FOREIGN PATENT DOCUMENTS

EP   0356896   1/1994

(Continued)

OTHER PUBLICATIONS

Muscarella, L., AAMI STWG61 Chemical Sterilants Hospital Practices Working Group, Association for the Advancement of Medical Instrumentation, AAMI TIR7:1999, Arlington, VA.

(Continued)

*Primary Examiner*—Gregory R. Del Cotto
(74) *Attorney, Agent, or Firm*—Quarles & Brady LLP; Gavin J. Milczarek-Desai

(57) ABSTRACT

Methods and apparatus utilizing supplemental ozone treatment for ensuring sterility of instrument cleaning systems. By flushing ozonated water through the components of a cleaning system, the persistent problem of contamination of cleaner chambers, pipes or lines, and filters or banks of filters is effectively prevented. Thus, the integrity of sterilized instruments, such as lumened medical instruments, is more reliably achieved and maintained.

9 Claims, 3 Drawing Sheets

U.S. PATENT DOCUMENTS

| | | |
|---|---|---|
| 6,448,062 B1 | 9/2002 | Huth et al. |
| 6,482,370 B2 | 11/2002 | Holsclaw et al. |
| 6,632,291 B2 | 10/2003 | Rabon et al. |
| 2002/0127158 A1 | 9/2002 | Holsclaw et al. |
| 2002/0141915 A1 | 10/2002 | Holsclaw et al. |

FOREIGN PATENT DOCUMENTS

| | | |
|---|---|---|
| EP | 0470116 | 12/1994 |
| EP | 06664715 | 9/1996 |
| WO | WO 00/02595 | 1/2000 |
| WO | WO 01/58500 A1 | 8/2001 |
| WO | WO 02/32467 A1 | 4/2002 |

OTHER PUBLICATIONS

Outpatient Surgery Magazine, Hospital, Sterilizer Manufacturer Debate Responsibility for Deadly Bacterial Outbreak.

Appleby, Julie, Widely Used Sterilizer Under Attack, USA Today, Jan. 21, 2003.

Outpatient Surgery Magazine, Hospital, Sterilizer Manufacturer Debate Responsibility for Deadly Bacterial Outbreak, 1999.

* cited by examiner

SUPPLEMENTAL OZONE TREATMENT FOR ENSURING THE STERILITY OF INSTRUMENT CLEANING SYSTEMS

REFERENCE TO RELATED APPLICATIONS

This application claims priority to PCT Patent Application No. PCT/US03/12027, filed 18 Apr. 2003, by the same inventor.

BACKGROUND OF THE INVENTION

1. Field of the Invention

This invention relates generally to methods and apparatus used to ensure that cleaned items are substantially free of biological and/or chemical contaminants and more particularly to methods that are especially useful to ensure the sterility of lumened medical items such as endoscopes.

2. Description of the Related Art

The cleaning and decontamination of items that come into contact with the bodily substances of people or animals such that they are substantially "substance free" (of, e.g., viruses, bacteria, detergent, sterilant, lipids, etc.) represent an immense and ongoing challenge. This challenge has been underscored by a recent article entitled "Widely used sterilizer under attack" (published in Jan. 21, 2003 edition of the newspaper *USA Today*). The article describes a fatal outbreak of bacterial infection that was linked to the improper sterilization of hospital bronchoscopes. Despite the hospital's use of one of the most popular sterilizing systems, tests performed by the Centers for Disease Control and Prevention found bacteria on the system's water filters and in its rinse water. This and other infection outbreaks has led to continuing controversy over how best to clean and sterilize used endoscopes.

The contaminants typically found on tubular or "lumened" medical items, such as endoscopes, are especially difficult to remove. In addition to fecal mater, loose cellular debris, blood and blood products, viruses, and bacteria, an endoscope can be coated with various hydrophobic films, such as "biofilm" material. A biofilm typically comprises cells, both dead and alive, cell debris and extracellular polymer substances. Once biofilm is formed by microorganisms (including bacteria, fungi, and protozoans), these microorganisms can colonize and replicate on the interior surfaces of tubing, forming a protective slime layer known as a "glycocalyx" that is especially difficult to remove.

Merely soaking endoscopes in a sterilant or detergent is unacceptable since numerous pockets exist within the tubing where the sterilant or detergent cannot reach effectively, which leaves areas of contamination within the endoscope. Moreover, with the prevalence of highly contagious diseases such as hepatitis B and C and Acquired Immune Deficiency Syndrome, reliable sterilization or disposal of all used medical tools seemingly becomes mandatory. Yet, while many medical instruments today are routinely cleaned, disinfected, and reused, experts in the field recently have warned that some of the more difficult to clean and sterilize medical items are putting people at risk.

Indeed, one expert has stated that there are no independent published reports or data anywhere in the medical literature that show liquid chemical sterilants (or any other method/process/agent) can be used to reliably "sterilize" flexible endoscopes or other complex, lumened instruments (See Comments by L. Muscarella (Custom Ultrasonics) on AAMI TIR7:1999, Chemical Sterilants and Sterilization Methods: A Guide to Selection and Use, downloaded from the website myendosite.com).

To the contrary, Kovacs et al. reports that a strain of *Pseudomonas aeruginosa* has been repeatedly isolated from tap water used for cleaning and rinsing endoscopes and appears to be responsible for three separate clinical episodes of endoscopic retrograde cholangio-pancreatography (ERCP)-associated cholangitis over an 11-yr period. These authors also conclude that the organism is resistant to a commonly used sterilant because it was recovered from a variety of endoscopes that had undergone stringent reprocessing protocols (see Kovacs B J, et al. "Efficacy of various disinfectants in killing a resistant strain of *Pseudomonas aeruginosa* by comparing zones of inhibition: Implications for endoscopic equipment reprocessing," *Am J Gastroenterol* 1998;93:2057-9). Thus, there is a genuine need for "overkill" sterilization to help ensure that even chemical-resistant pathogens are effectively eliminated.

In addition to the infection issues, environmental concerns over the content of medical item wash or rinse water effluent have become more pronounced as the detrimental effects (including toxicity) of various cleaning and sterilizing chemicals are now better understood. For example, commonly used liquid chemical sterilants, such as glutaraldehyde and paracetic acid, are known to have adverse health effects or carcinogenic activity. Since most endoscope cleaning and sterilization is accomplished with various detergents in combination with glutaraldehyde or paracetic acid, harmful chemical residue can be left behind both on the item and in the wash or rinse effluent. Therefore, discharge of these chemicals into rivers, lakes, and even sewer systems raises safety issues that have yet to be addressed.

Furthermore, some chemical cleaners or sterilants are so harshly reactive that they can damage the items they are meant to clean or sterilize. Thus, the problems encountered during item (and especially medical item) cleaning and disinfecting primarily involve trying to strike a balance between ensuring as much as possible the complete removal of contaminants and chemicals while, at the same time, not damaging the instrument or the environment.

Even the simple act of rinsing medical items with filtered water after cleaning or sterilization has been called into question. After sterilization, endoscopes typically are rinsed with water filtered down to the 0.2 micron (200 nanometer) level. Unfortunately, many viruses, endotoxins, and prions are smaller than 200 nanometers, meaning that they can remain in the water even after filtration. Also, as reported in the articles mentioned above, water and water filters are known sources of contamination. Even more troubling, however, is the statement by one expert that "there are no independent data in the medical literature that support the production of sterile water (defined as containing fewer than $10^{-6}$ CFU/ml and fewer than 5 endotoxin units/ml) by passing unprocessed water (that is, unsterilized water, such as water that flows though a hospital's tap) through a bacterial (e.g., 0.1 or 0.2 micron) filtration system" (See Comments by L. Muscarella (Custom Ultrasonics) on AAMI TIR7:1999, Chemical Sterilants and Sterilization Methods: A Guide to Selection and Use, downloaded from the website myendosite.com). Moreover, there is no currently available system that monitors the biological content of filtered water to insure its sterility when used in conjunction with medical item cleaning or sterilization apparatuses. Finally, having to add additional sterilization steps and/or use sterilized (e.g., autoclaved) water becomes tedious and expensive.

Ozone is a well known sterilant. Ozone was first used for drinking water treatment in 1893 in the Netherlands. While being used frequently in Europe for drinking water disinfection, it was slow to transfer to the United States. Indeed, early application of ozone for water treatment in the United States was primarily for non-disinfection purposes such as color removal or taste and odor control. Today, ozone also is known to oxidize oils and reduce scale build-up. Nonetheless, the strongly oxidative qualities of ozone also present problems in that the use of ozone for the cleaning and disinfecting of items will often result in permanent damage to the item, especially if it is exposed to ozone for long periods while attempting to completely clean and decontaminate all surfaces.

Thus, while ozone applications to water and water line disinfection are now fairly common, these methods have not become widespread in other sterilization applications because they rely on a treatment system that reticulates ozonated water through the entire treatment area during repeated cleaning cycles in order to achieve and maintain disinfection. Such constant treatment is not possible for most items (and especially medical items) due to the damage that continual or repeated exposure to ozone would cause.

Even with recent advances in cleaning devices and methods, such as those invented by Langford (see, for example, U.S. Pat. No. 5,443,801), there still remains the problem of balancing the need for complete cleaning, disinfection, and degradation of all chemical residues on an item with preventing or mitigating damage to that item and to the environment.

Therefore, there continues to be a need for a cleaning and decontaminating method that, without damaging the item being treated, helps to ensure sterility, assists in loosening difficult soiling, such as biofilm-entrained contaminants and other hydrophobic compositions or films, and degrades chemicals so that effluent is substantially free of harmful residues.

SUMMARY OF THE INVENTION

The invention generally involves methods for flushing the components of an instrument cleaning/sterilizing system with ozonated water as a supplement to conventional filtration and cleaning/sterilization regimens. Apparatus having a means for introducing ozone into a cleaning/sterilizing system, which is preferably done through a separate re-circulating water reservoir, are also described.

In one aspect of the invention, ozonated water is not used as a primary cleaning or sterilizing agent for the instrument undergoing treatment. Instead, ozone treatment is used as an "insurance" or "overkill" measure to ensure that the cleaning system itself is not re-introducing undesirable matter to the instrument(s) being cleaned or sterilized within through contaminated system components, such as filters, lines, or cleaning chambers.

The general concept is that treating a cleaning/sterilizing system with ozone as a supplemental initial, intermediate, and/or final treatment step, in cooperation with one or more other chemicals used to actually clean and sterilize a specific instrument, ensures that the instrument and effluent are free of infectious agents that could have been introduced by contamination harbored within the system itself. Given the recent focus on the need to provide an "overkill factor" to prevent re-contamination of endoscopes and other medical or dental equipment, the invention provides for the ozonation of the filters commonly used to filter water used within the cleaning/sterilizing system.

An added point of novelty of this invention is that supplemental ozone treatment facilitates the use of very effective yet non-preferred cleaning agents and sterilants. For example, the European Union and Australia have recommended against the use of glutaraldehyde for sterilizing endoscopes due to pollution and exposure-based heath concerns. By adding ozone treatment to the end of the glutaraldehyde sterilization process, harmful chemical residue is degraded.

Accordingly, in one embodiment of the invention, a method of using ozonated fluid is provided as a "pre-rinse" to solubilize hydrophobic residue (e.g., biofilm deposits), thereby making the cleaning/sterilizing process more efficient. In other words, the invention involves a new and improved method of using ozone as a "pre-rinse" to loosen soil such that further cleaning and sterilizing would be more effective. Preferably, the item to be cleaned or sterilized is pre-rinsed by having ozonated fluid pass back-and-forth over the exterior and through any openings in the item. In another embodiment, a "final rinse" of a medical item is made with ozone to prevent re-contamination and to degrade chemical sterilant and cleaning chemical residue on the item and in the effluent, thus allowing the discharge of the same into the sewer. Still other embodiments feature co-treatments of ozone and cleaning or sterilizing agents.

Thus, it is a primary objective of the invention to provide a medical item cleaning method that improves cleanliness and ensures sterility while rendering the effluent substantially harmless.

Further, an object of the invention is to provide a cleaning method that effectively utilizes ozone while minimizing damage to the item being cleaned.

Yet another object of the invention is to provide a cleaning method that is adaptable for use in supplementing currently existing cleaning methods.

An additional object of the invention is to provide a cleaning method that is economical and inexpensive to utilize.

Still another object of the invention is to provide a cleaning and sterilizing method that may be used in conjunction with a wide variety of cleaning or sterilizing apparatuses.

Yet another object of the invention is to provide a method and apparatus for ensuring the sterility of cleaning system components, such as filters, so that contaminants are not re-introduced to an instrument after cleaning and sterilization have taken place.

In accordance with these and other objects, there is provided new and improved supplemental ozone treatment methods and apparatus. The method is especially useful in the treatment of water entering an apparatus used to clean and sterilize a lumened instrument by providing an "overkill" effect that prevents re-contamination of the instrument and the cleaning/sterilizing apparatus, including any water filter used therewith.

Various other purposes and advantages of the invention will become clear from its description in the specification that follows. Therefore, to the accomplishment of the objectifies described above, this invention includes the features hereinafter fully described in the detailed description of the preferred embodiments, and particularly pointed out in the claims. However, such description discloses only some of the various ways in which the invention may be practiced.

DETAILED DESCRIPTION OF THE PREFERRED EMBODIMENTS

The invention relates generally to a method for treating soiled instruments that combines ozone treatment with cleaning and/or sterilizing treatments involving one or more chemical agents. The invention also relates to the use of ozone treatment for ensuring the sterility of a cleaning/sterilizing equipment or system. In other words, ozone is not used as a primary cleaning or sterilizing agent, but, rather, ozone treatment is provided only to supplement other cleaning/sterilizing agents or as an "overkill" treatment for system components. Thus, the problems associated with ozone use (e.g., oxidative damage) are overcome while beneficial results are produced.

The terms "cleaning/sterilizing apparatus," "cleaning/sterilizing system," or "cleaning apparatus," "sterilizing apparatus," and "reprocessor" as used throughout the specification are meant to be synonymous and include an apparatus (such as the Steris™ System 1 and Langford IC Systems, Inc. Manzi Mark 1) that either cleans, sterilizes, or cleans and sterilizes instruments coming in contact with the body (e.g., endoscopes, dental appliances, and the like).

Figure 1:
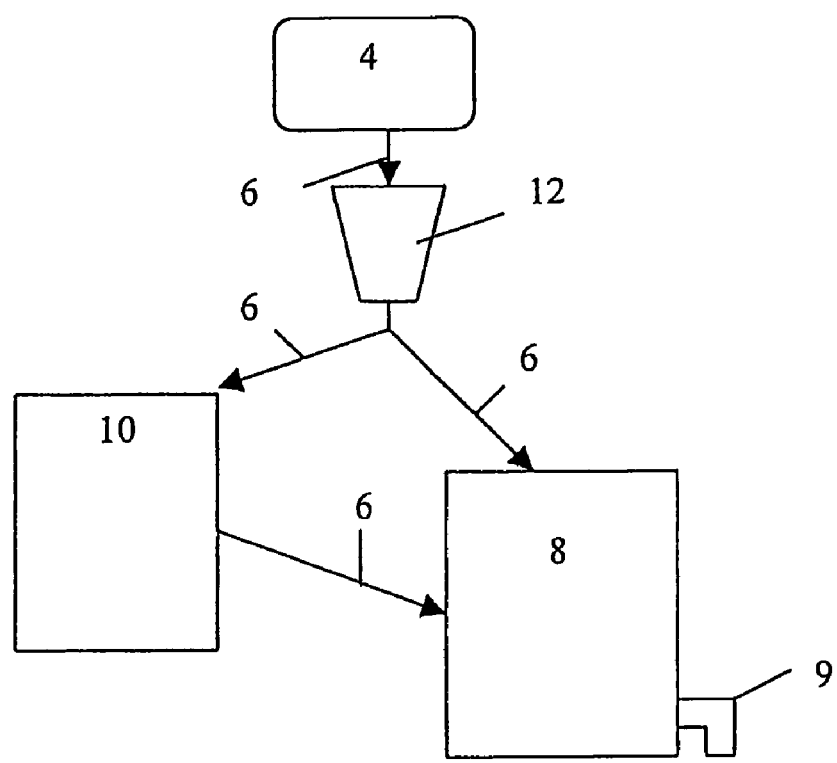
FIG. 1 schematically illustrates a prior art cleaning/sterilizing apparatus.

Turning to the figures, wherein like numbers indicate like structures throughout the specification, a prior-art cleaning/sterilizing apparatus 2 is shown in simplified schematic form in FIG. 1. A water source 4 (typically tap water) is in fluid connection (designated by arrows 6, which may be pipes, tubes, and the like) with a instrument cleaning chamber 8 having a fluid exhaust port 9. Although not explicitly shown, it should be understood that valves may be installed at any junction point, such as where an arrow branches or meets a filter, reservoir, chamber, or another arrow. Thus, the flow of fluids can be made optimally controllable by the system operator.

A water reservoir 10 may be included in the system 2 to provide readily available hot water and the like. In order to economize and for ease of operation, water from source 4 is filtered through filter 12 to avoid the use of autoclaved water and so forth. As discussed above (and demonstrated in Example 4 below), problems with the filtration system of a cleaning/sterilizing system can lead to the rinsing of instruments placed within the chamber with contaminated water.

Figure 2:
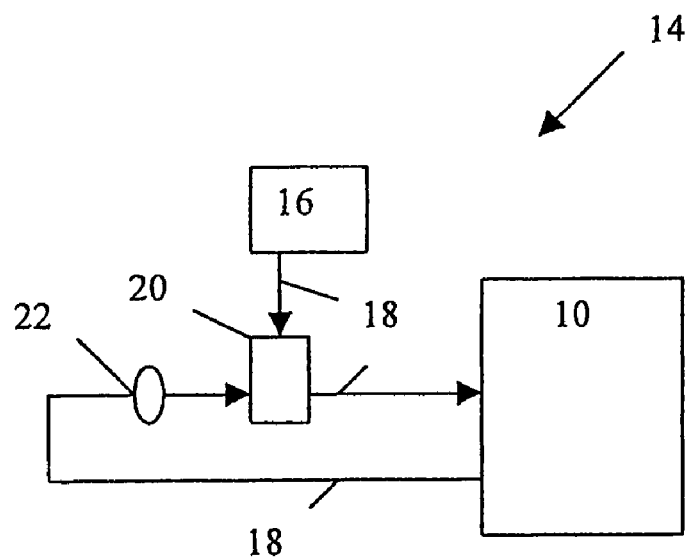
FIG. 2 schematically illustrates a means for introducing ozone into a cleaning/sterilizing apparatus according to the invention.

Thus, as seen in FIG. 2, a preferred embodiment of the invention includes an ozonation loop 14 that can be added to an existing system (e.g., to the reservoir 10 of FIG. 1). The loop 14 features an ozone generator 16 in fluid connection 18 with reservoir 10. Ozone is added to the water in the reservoir 10 through venturi 20. Preferably, a re-circulating pump 22 is used to continuously introduce ozone into the water of reservoir 10, thereby ensuring sterility of the water after a predetermined amount of time of ozone treatment (i.e., depending on the volume of water, temperature, pressure and so forth).

Accordingly, a method for ensuring sterility in a cleaning/sterilizing system for an instrument includes introducing ozone into water from an inlet source to form sterilized water and circulating the sterilized water through the cleaning and/or sterilizing system. Preferably, the sterilized water is formed by introducing ozone into water contained by a reservoir in fluid connection with the instrument cleaning system and the reservoir is pressurized or chilled to ensure good ozone solubility. Also preferably, ozone is introduced to the water within the cleaning/sterilizing system before that water contacts any filter or instrument being cleaned and sterilized.

Figure 3:
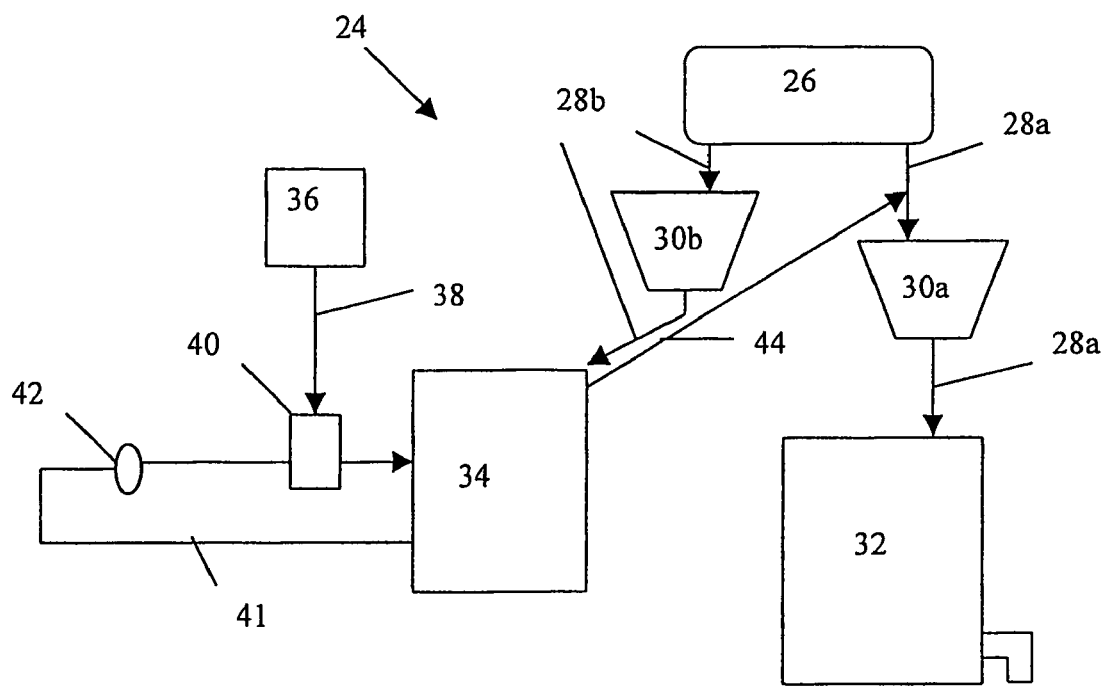
FIG. 3 schematically illustrates a first embodiment of a cleaning/sterilizing apparatus of the invention.

Thus, in a further embodiment of the invention, a schematic illustration of a complete cleaning/sterilizing system 24 is shown in FIG. 3. Water inlet source 26 is fluidly connected as shown by arrows 28a and 28b to filters 30a and 30b, as well as to chamber 32 and reservoir 34. Reservoir 34 holds water that is ozonated by ozone generator 36 through fluid connection 38 to venturi 40. Fluid connection 41 takes water from reservoir 34 and re-circulate it via pump 42 through venturi 40 to ensure that a sterile water supply is readily available for use in the chamber 32.

In a typical cleaning cycle, filtered water is used in combination with detergent. A chemical sterilant is then added to the system and must be rinsed out. Thus, sterile, ozonated water will flow through fluid connection 44 to provide a final rinse of not only the chamber 32 and the instrument (not shown) being cleaned, but also of the filter 30a. Since previous cleaning/sterilizing systems used only filtered water to accomplish this final rinse, re-contamination was possible (and has been documented). Utilizing ozonated water provides an "overkill" factor that ensures everything remains sterile.

In addition, a sterile rinse of filter 30a (as well as a flush of the entire cleaning/sterilizing system) may be performed with ozonated water before an instrument is placed within the cleaning chamber or periodically during times in which the system is not in use in order to prevent the growth of organisms lodged within the system (e.g., trapped in the filter).

Figure 4:
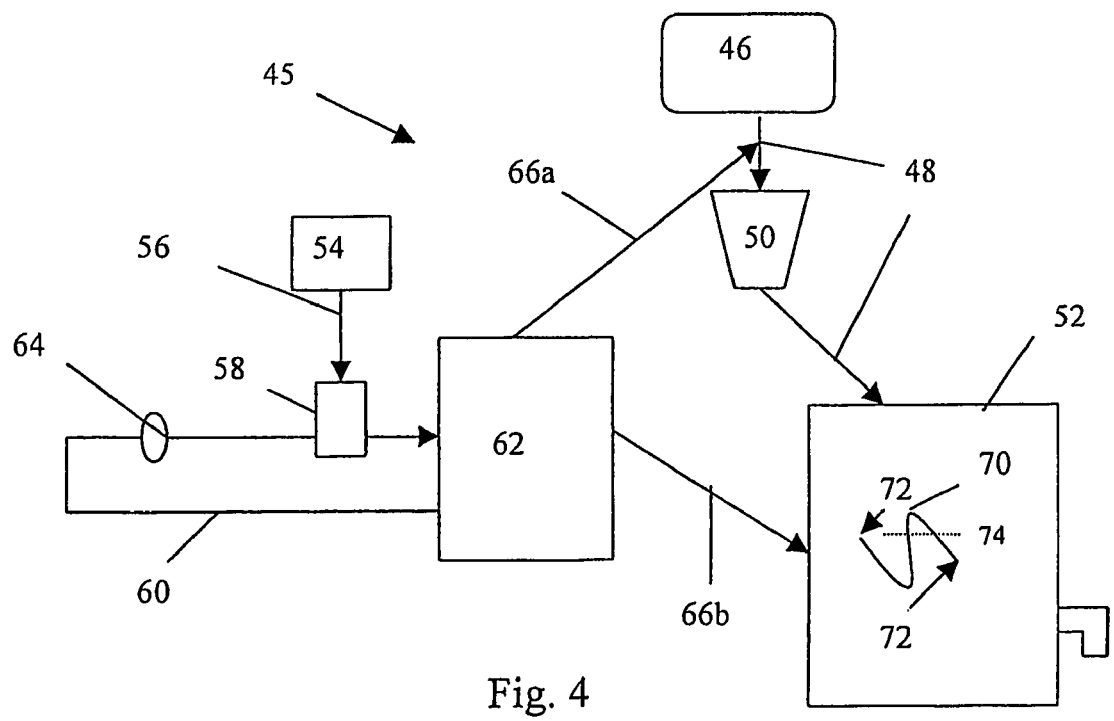
FIG. 4 schematically illustrates second embodiment of the invention.

Turning to FIG. 4, a third embodiment of the invention is schematically depicted. The cleaning/sterilizing system 45 includes a water source 46 in fluid connection (arrows 48) with filter 50 and chamber 52. Ozone generator 54 is connected via pipe or tube 56 to venturi 58, which provides ozone to water in fluid connector 60 and water reservoir 62. Re-circulation of the ozonated water is accomplished through pump 64. The ozonated water in reservoir 62 and can be provided to chamber 52 either fluid connection 66a or directly though fluid connection 66b. Shown inside chamber 52 is an instrument 70 (in this case an endoscope). Because contamination of any structure that is direct contact with the soiled ends 72 of instrument 70 can persist and contaminate subsequently washed instruments, preferably the instrument 70 is mounted in the chamber 52 in a "connector-less" fashion through holder 74. The holder 74 may take the form of a simple clamp. Thus, unlike the narrow tubes used in other systems to inject liquid through the ends of an instrument, the ends 72 are not connected to any part of the chamber that might serve as a harbor for microbes.

Alternatively, for especially difficult cleaning application, such as soiled lumened instruments, an instrument can be pre-treated outside of the cleaning apparatus by injecting a liquid (preferably a colored liquid) thru an end to determine whether a blockage exists within the lumen. If a blockage does exist (i.e., no liquid comes out the other end), a filament may be run through the instrument prior to the wash cycle being performed to insure that blockages do not interfere with complete cleaning and sterilization.

An important advantage of the preferred design of the invention is that sterilized water is formed and stored in the reservoir while a wash process occurs. In other words, sterile water is made in parallel with other operations such that not time is lost because the sterilized water is ready for use after the parallel process is complete. Of course, the sterile water can be used at other times as well, such as to circulate throughout and, thereby, "flush" the system clean of contaminants after a period of inactivity.

Figure 5:
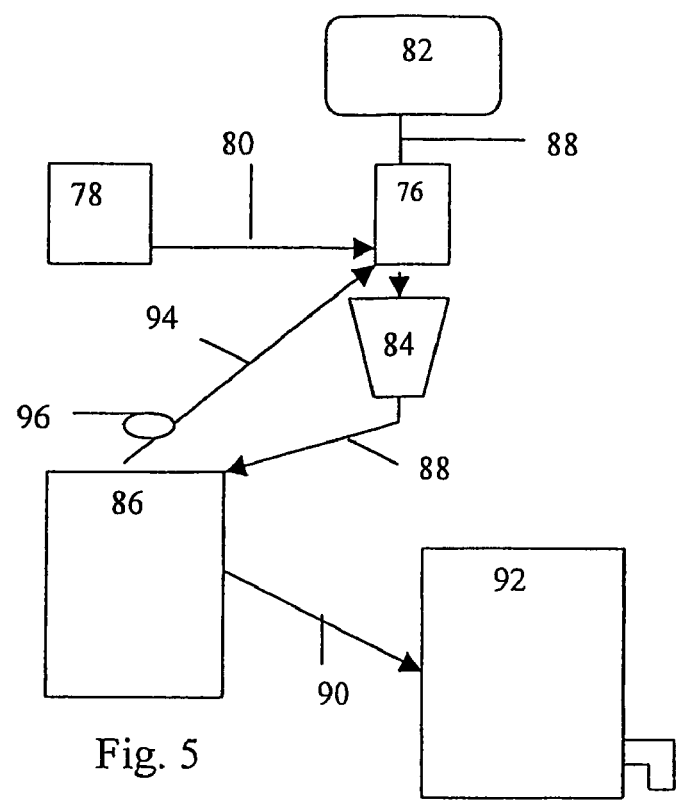
FIG. 5 schematically illustrates a third embodiment of the invention.

FIG. 5 schematically illustrates a basic embodiment of the invention in which a venturi 76 is connected to an ozone generator 78 by a fluid connection 80. Venturi 76 ozonates water from the water inlet 82 before it passes through filter 84 and on to reservoir 86 through fluid connection 88. Fluid connection 90 allows only ozonated and filtered water to pass through to chamber 92. Fluid connection 94 and pump 96 provide a means for recirculating ozonated water to ensure ozone content sufficient for sterility.

The synergistic effects produced by combining ozone with other chemical treatment regimens greatly increases cleaning and sterilizing options. For example, effective cleaning and sterilizing substances that currently are not widely used due to health and pollution concerns can now be utilized because virtually any chemical will be degraded when exposed to ozone. The synergistic benefits of providing ozone treatment with other chemical agents also extend to difficult cleaning applications. Indeed, one of the main problems with cleaning agents in use today is that they do not efficaciously remove the "greasy residue," such as cellular lipids, fat particles, or biofilm. However, despite the industry-wide reservations to ozone use (due to the damage prolonged exposure can cause to medical items), the inventor has discovered that ozone treatment in combination with existing cleaning and sterilizing methods can solve this and other problems in order to advance the methods of the art.

Accordingly, in some embodiments of the invention, ozone is used as a "pre-soak" or "pre-rinse" to help break down or loosen soil, such as proteins, lipids, or other hydrophobic biomatter. In other embodiments, combinations of ozone with cleaning agents are used to clean and degrade contaminants and chemical residue. In still other embodiments, an item is first cleaned using, for example, a detergent. Afterwards, a sterilant is applied and then removed with a rinse of ozone (e.g., ozonated water) washed over and through the endoscope in preparation for subsequent use with a patient. Still another embodiment involves treating rinse water with ozone to prevent re-contamination of the item.

Within this discussion, endoscopes will be used as an example of an item or instrument to be cleaned. However, the invention is not intended to be limited to this one type of item. Rather, the inventor contemplates use of the invention with any tubular item as well as a variety of other items such as circuit boards, medical instruments, dental instruments, and other items in which reliable cleaning and/or sterilization is required.

Ozone exists as a gas at room temperature. The gas is colorless with a pungent odor readily detectable at concentrations as low as 0.02 to 0.05 ppm (by volume), which is below concentrations of health concern. Ozone is a powerful oxidant, second only to the hydroxyl free radical, among chemicals typically used in disinfecting treatments. Therefore, it is capable of oxidizing (and thereby damaging) many organic and inorganic compounds used in medical items, such as endoscopes.

Ozone is sparingly soluble in water. At 20° C., the solubility of pure ozone is only 570 mg/L. Ozone concentrations used in water treatment are typically below 14 percent, which limits the mass transfer driving force of gaseous ozone into the water. Consequently, typical concentrations of water-soluble ozone range from <0.1 to 1 mg/L, although higher concentrations can be attained under optimum conditions.

Basic chemistry research has shown that ozone decomposes spontaneously in water by a complex mechanism that involves the generation of hydroxyl free radicals. The hydroxyl free radicals are among the most reactive oxidizing agents in water, with reaction rates on the order of 1010-1013 $M^{-1}s^{-1}$, approaching the diffusion control rates for solutes such as aromatic hydrocarbons, unsaturated compounds, aliphatic alcohols, and formic acid. On the other hand, the half-life of hydroxyl free radicals is on the order of microseconds. Therefore, concentrations of hydroxyl free radicals can never reach levels above 10-12 M.

Chemically speaking, ozone can react either by direct oxidation of compounds by molecular ozone ($O_3$(aq)) or by oxidation of compounds by hydroxyl free radicals produced during the decomposition of ozone. The two oxidation pathways compete for substrate (i.e., compounds to oxidize). The direct oxidation with aqueous ozone is relatively slow (compared to hydroxyl free radical oxidation) but the concentration of aqueous ozone is relatively high. On the other hand, the hydroxyl radical reaction is fast, but the concentration of hydroxyl radicals under normal ozonation conditions is relatively small.

Under acidic conditions, the direct oxidation with molecular ozone is of primary importance; and under conditions favoring hydroxyl free radical production, such as high pH, exposure to UV, or addition of hydrogen peroxide, the hydroxyl oxidation starts to dominate. The spontaneous decomposition of ozone occurs through a series of steps. The exact mechanism and reactions associated have not been established, but mechanistic models have been proposed. It is believed that hydroxyl radicals form as one of the intermediate products, and can react directly with compounds in the water. The decomposition of ozone in pure water proceeds with hydroxyl free radicals produced as an intermediate product of ozone decomposition, resulting in the net production of 1.5 mole hydroxyl free radicals per mole ozone.

Because ozone is an unstable molecule, it should be generated at the point of application. It is generally formed by combining an oxygen atom with an oxygen molecule. This reaction is endothermic and requires a considerable input of energy. Ozone can be produced several ways, although one method, corona discharge, predominates in the ozone generation industry. Ozone can also be produced by irradiating an oxygen-containing gas with ultraviolet light, electrolytic reaction and other emerging technologies. Most ozone generators currently use ultraviolet radiation. These are usually the lowest cost ozone generators on a per unit basis. This decrease in cost is due to the fact that the air does not go through an initial drying process.

Newer units being produced utilize a corona discharge technique which dry the air before charging the air with ozone. This drying permits the corona discharge apparatus to produce a higher ozone concentration. For minimal expenditures of electrical energy, ozone normally is produced from dried air (−60 degrees Fahrenheit dew point) in concentrations of one to two percent and from dry oxygen in concentrations of two to four percent. More than eighty percent of the electrical energy applied to the electric discharge field is converted to heat and, if this is not quickly removed from the cell, the heat causes rapid decomposition of the ozone back to oxygen. For additional guidance in ozone production and its uses, see U.S. Pat. No. 5,207,237.

For cleaning or sterilizing methods involving the use of ozone, it is important to recognize that the time of exposure and concentration of ozone will vary based on a number of parameters, such as the quantity and size of items being treated, the volume of the cleaning or sterilizing apparatus, and the nature and amount of "soil" on and in the item. Preferably, ozonated water is used to treat items for 5-30 minutes at a concentration of 1-10% ozone by volume.

In terms of checking the progress of ozone-assisted cleaning, existing standards used for monitoring cleaning efficacy before passing from the wash/rinse cycle of a given cleaning apparatus would be chosen to meet the standards of the time or the situation. The preferred standard is set forth by the Food and Drug Administration, including flow-rate and size of particles found in Particulate Matter in Injections, commonly known as USP 788 Specification.

A number of known cleaning and sterilization methods are readily available. Some are performed in automatic endoscope reprocessors, while others are done manually. For example, Yale Medical School recommends that an endoscope can be manually cleaned by placing the distal end of the endoscope into an enzymatic detergent solution followed by applying suction to the solution through the biopsy/suction channel until the solution is visibly clean. One then alternates the suctioning of clean detergent solution with air several times, followed by removing the air under vacuum (further details are available online at Yale's Internet website info.med.yale. edu/ynhh/infection/steril/standards). To supplement this cleaning method, ozonated water (2% by volume) could be used to pre-rinse (preferably, by moving the ozonated water over and through the endoscope continuously) for 5 minutes before the washing protocol is implemented in order to loosen the soil in and on the endoscope. Alternatively, five minutes of ozonated water washing could be substituted for the final "clean detergent solution" rinse to degrade residual detergent before sterilization commences.

The following additional examples are meant to further illustrate, but not to limit, the invention.

EXAMPLE 1

1. Purpose

The purpose of this test is to document the results of engineering characterization testing performed on a automatic endoscope reprocessor, the Langford I.C. Systems Sterilizer Cleaner (see U.S. Pat. No. 5,906,802 for layout and guidance in the use of this reprocessor). This test is intended to determine that a test lumen scope is clean by visual inspection only (Example 2 describes a test to quantify the level of sterility).

2. Scope

This test seeks to describe methods and test results for cleaning efficacy of individual and combined cycle phases on mock devices used to simulate a colonoscope. Testing was performed on DWGX-0129-01888, Cleaner, Sterilizer Breadboard.

3. Equipment and Calibration 4.1 EQP-0129-0001, Thermocouple Omega Model HH21 Type J, K, T.

4.2 Birmingham simulated respiratory tract soils 4.3 Hucker's simulated fecal soil 4.4 SIMPLE GREEN cleaner (Sunshine Makers, Inc)

4.5 LESTOIL concentrated cleaner (The Clorox Company)

4.6. Digital camera 4.7 250 ml plastic graduated cylinder 4.8 Device under test a. DWGX-0129-01888, Cleaner Sterilizer Apparatus Breadboard b. DWGX-0129-01889, Mock Colonoscope Assy 5. Test Description Testing was conducted to determine initial parameter settings necessary for effective cleaning of Birmingham soil and Hucker's soil from mock scope and simulated scope lumens. The scope lumens and mock scope were inoculated with either the Birmingham soil or the Hucker's soil (at a level that is 100× the level of soiling required FDA test standards) and left sitting for a one hour time period to permit some drying. In this test, we determined cleaning effectiveness by visual inspection only. This was done by running the Sterilizer Cleaner machine with varying baffle configurations, temperatures, cleaners (type and quantity), speed and time.

After a test was completed, the resulting pressure was recorded on the log sheet along with test results. Depending on the effectiveness of the first cycle of the test, a second clean cycle was run to show the mock lumen or mock scope was clean by visual inspection. Other times a first clean cycle was run and a second rinse (water only) cycle was run to further clean the test lumen or scope. After the test Lumen or scope was clean by visual inspection, a digital picture was taken and stored for future reference. The test lumen then was bagged and tagged and stored for future reference.

6. Test Results and Conclusions

The Langford I.C. Systems Sterilizer Cleaner performed effectively at cleaning out both Birmingham soil and Hucker's soil from the exterior and the interior of mock lumens and the mock scope. The two cleaning agents were used and seemed to be equally effective. The Langford I.C. Systems Sterilizer Cleaner performed effectively at pressures as little as 4 psi and at temperatures as low as 110° F. for washes or rinses of as little as 5 minutes in length. The preferred rate of "liquid displacement" (i.e., the back-and-forth liquid cycling rate in the item-washing chamber of the Sterilizer Cleaner) is 1 gallon per 2 seconds. Based on these results, a number of different cleaning protocols may be used successfully. One preferred protocol involves using 250 ml of SIMPLY GREEN detergent to wash the endoscope for 5 minutes at 110° F. and 5 psi on the 1 gallon/2 seconds liquid-displacement setting, followed by a water rinse at the same temperature and pressure.

7. Supplement: Adding Ozone Treatment a. Prior to the first cleaning cycle with a detergent, the mock scopes are exposed to ozonated water (4% by volume) at a liquid-displacement rate of 1 gallon/2 seconds for 5 minutes to loosen soil. The ozone is generated by corona discharge and added to water in the chamber fill line thru a Mazzei venturi injector at a rate of 1.25 g/hr at 5 SCFH dry air flow (per an 11 gallon system, but can be adjusted for other volumes). After ozone exposure, the scopes are cleaned using 250 ml of SIMPLY GREEN detergent and washing for 5 minutes at 110° F. and 5 psi on the 1 gallon/2 second liquid-displacement setting, followed by a water rinse at the same temperature and pressure.

b. After the cleaning cycle is complete, the rinse water is ozonated by corona discharge as described above in step a. The mock scopes are then rinsed with the treated water for 5 minutes to degrade any residual detergent.

EXAMPLE 2

The biopsy lumen of three colonoscopes were loaded with Hucker's Soil (100× more than required by FDA test standards) and inoculated with pathogens from an American Society of Test Methods kit. The scopes were left sitting for a 24 hour time period to permit some drying. Using the same Langford I.C. Systems Sterilizer Cleaner liquid-displacement settings as in Example 1, each colonoscope was subjected to one detergent wash at 4 psi for 10 min with 250 ml of SIMPLE GREEN cleaner in 10 liters of water followed by three 5 min rinses with 10 liters of filtered tap water. For the last (third) rinse, ozone generated by corona discharge was added to the water thru a Mazzei venturi injector connected to the incoming water line of the Langford reprocessor apparatus. The ozone was added to the water at a rate of 1.25 g/hr at 5 SCFH dry air flow.

Tests performed to quantify the level of decontamination on the three mock scopes used in this example indicated that two of the scopes showed a log $10^{-5}$ pathogen kill while one scope had log $10^{-6}$ pathogen kill (indicates sterility). Visual inspection revealed no apparent damage to any endoscope surface.

Especially given the extremely high level of soiling, these results are much better than has previously been achieved for any known cleaning/disinfecting protocol, which typically results in a less than log $10^{-3}$ pathogen kill. Hence, supplementing existing endoscope reprocessing methods with ozone treatment results in a quantitative difference in decontamination without damage to the endoscope.

EXAMPLE 3

In this example, a partitioned cleaning and sterilizing device of the type described and illustrated in U.S. Pat. No. 5,711,921 is utilized. The endoscope is positioned to extend through the partition such that one opening of the endoscope lies in one chamber and another opening of the endoscope lies in the other chamber. The partition between the chambers need not be an absolute partition and, in this example, the partition fits loosely around the endoscope so that as the medium (i.e. a liquid detergent, sterile water, a liquid sterilant, or a sterilant gas) surges from one chamber to the other, the medium washes over the exterior of the endoscope and simultaneously sweeps through the interior of the endoscope. The device creates this "surge" through the use of one or more flexible membranes. By deforming the flexible membrane (inward and outward), a pressure or suction is created which results in a flow (liquid displacement) between the chambers to equalize the pressure between them.

250 ml of detergent is added to 10 liters of water and is used to wash the endoscope for 10 min. The scope is then rinsed twice for 5 minutes each with 10 liters of filtered tap water. After the last water rinse, 10 liters of a liquid chemical sterilant (preferably 1 ounce paracetic acid per 5 liters of water) are added to the cleaner/sterilizer and the endoscope is washed for 5 minutes. Those of ordinary skill in the art readily recognize various other sterilants which can be used in this context.

In order to degrade any sterilant residue and to provide a final "overkill" treatment to prevent re-contamination of the endoscope (and the filter, cleaning chamber, or ports of the reprocessor equipment) by the filtered water, a final rinse with 10 liters of water ozonated at 1 g/hr at 5 SCFH dry air flow is performed for 5 minutes. Alternatively, the overkill treatment with ozonated water is provided by ozonated, filtered water stored in tank. The ozone is continuously added to the water in the tank by re-circulation past the venturi. Thus, the sterility of the water is ensured without exposing the reprocessor components or items to be cleaned to a constant supply of freshly generated ozone.

It should now be readily understood that ozone or an ozonated fluid could be used prior to, concurrent with, or after the cleaning steps described in order to improve cleaning and/or breakdown the detergent. Likewise, ozone or an ozonated fluid could be applied prior to, concurrent with, or after a chemical sterilant. Preferably, at least the final rinse water used in any protocol should be ozonated at the point of application to prevent re-contamination of the cleaned and sterilized item. This is especially true if the sterilization method relies on the use of filtered tap water.

EXAMPLE 4

A protocol was devised to test the ability of ozone to produce sterile water from inoculated tap water that had been filtered using a Langford IC Beta unit 0.22µ filtration system. The test protocol called for three individual biological challenges to test a broad range of sterilization potentials by including *Bacillus subtilis, Pseudomonas aeruginosa,* and *Candida albicans* to cover spore, bacterial and fungal organisms.

Figure 6:
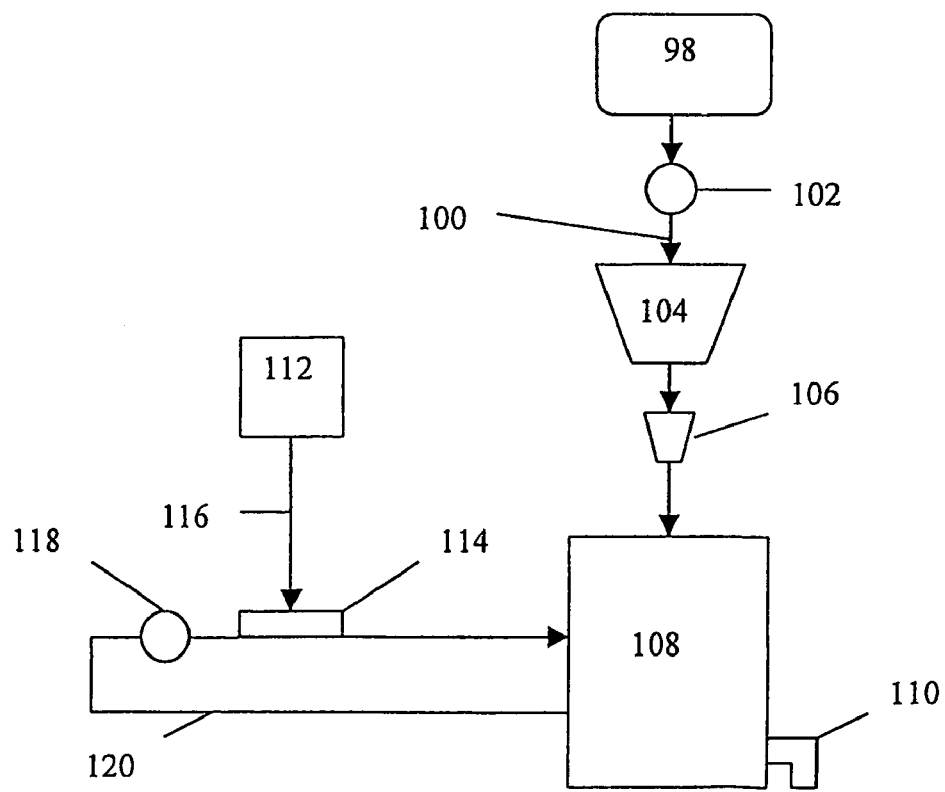
FIG. 6 schematically illustrates a testing set-up as described in Example 4.

The equipment used included a Clear Water Tech ozone generator model CD-10 AD with a model 584 Venturi, a Finish Thompson re-circulation pump model AC4ASTS, a six gallon polypropylene tank, a Hanna ORP controller model HI 8512 with a model HI 2931B/5 ORP electrode, an electronic thermometer, a stopwatch, and sample containers. As illustrated in FIG. 6, testing was conducted using an ozone re-circulation "test loop." A water source 98 was configured to be in fluid connection 100 with a pump 102, a bank of filters 104 (2 micron) and 106 (0.22 micron), and chamber 108 (where samples for measurement of organism content could be taken from exhaust port 110). Ozone generator 112, which was connected to venturi 114 by fluid connector 116, provided a means to treat water in the chamber 108 in a re-circulating fashion through pump 118 and fluid connection 120.

A positive control sample was taken prior to the dual filter stages to determine the initial bioburden level for each organism. A post-filtration sample was also taken to determine the filter efficacy prior to ozonation. Ozonation samples were taken at 15, 30, 45 and 60 minute intervals, while pump flow rates measured at 4.5 GPM.

The three test organisms were incubated for 7 days to ensure maximum growth potential and met the test requirement of at least $10^6$ Colony Forming Units (CFU)/100 ml. It should be noted that this high level of bioburden is far in excess of the levels typically found in municipal tap water (<500 CFU/ml as per the U.S. EPA).

The positive controls for each test organism confirmed that the pre-filtered water harbored between 3-9 million CFU per 100 ml. For two of the three organisms (*Pseudomonas aeruginosa,* and *Candida albicans*), post-filtration samples still harbored significant quantities of organisms (about 600,000 CFU/100 ml and about 40,000 CFU/100 ml, respectively). In contrast, all ozonated samples at the 15, 30, 45, and 60 min time points showed less than 1 CFU per 100 ml.

The test data demonstrate that supplemental ozone treatment of the cleaning system water effectively eliminated measurable bioburden, even during massive filtration failures (as demonstrated by the large *Pseudomonas aeruginosa,* and *Candida albicans* carryover). Thus, the prevention of contamination or re-contamination of an instrument being cleaned and sterilized is achieved.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products. All references cited in this application are hereby incorporated by reference herein.

I claim:

1. An apparatus for cleaning and sterilizing an instrument that comes into contact with a body, comprising:
    a chamber adapted to connectorlessly engage, through a holder, said instrument placed within said chamber during cleaning and sterilization, said chamber including a fluid exhaust port,
    a pressurized water reservoir in fluid connection with said chamber,
    a re-circulating water pump in fluid connection with said water reservoir,
    a water source in fluid connection with said water reservoir; and
    a means for introducing ozone into said water from the water source wherein said means is located prior to the introduction of said water into said reservoir,
    wherein said re-circulating water pump provides sterile water by re-circulating ozonated water within said reservoir.

2. The apparatus of claim 1, further including a filter means disposed between the water source and the pressurized water reservoir.

3. The apparatus of claim 2, wherein said ozone is introduced before the water contacts said filter means.

4. The apparatus of claim 1, wherein the water source is in fluid connection with both the pressurized water reservoir and the chamber.

5. The apparatus of claim 4, further including one or more filter means disposed between the water source, the pressurized water reservoir, and the chamber.

6. The apparatus of claim 1, wherein said chamber is pressurized.

7. The apparatus of claim 1, wherein said water includes between 0.1 and 15 percent ozone by volume.

8. The apparatus of claim 1, wherein said instrument comprises a lumened instrument.

9. The apparatus of claim 1, wherein said means for introducing ozone achieves a greater than log six reduction in any bacteria, spores, or fungi present within said apparatus.

* * * * *